United States Patent
Arnoldussen et al.

(10) Patent No.: US 8,292,878 B2
(45) Date of Patent: *Oct. 23, 2012

(54) OPERATOR-CONTROLLED SCANNING LASER PROCEDURE DESIGNED FOR LARGE-AREA EPITHELIUM REMOVAL

(75) Inventors: Mark E. Arnoldussen, San Carlos, CA (US); Jonathan Wong, Milpitas, CA (US); Benjamin A. Logan, San Jose, CA (US)

(73) Assignee: AMO Manufacturing USA, LLC., Santa Ana, CA (US)

( * ) Notice: Subject to any disclaimer, the term of this patent is extended or adjusted under 35 U.S.C. 154(b) by 38 days.

This patent is subject to a terminal disclaimer.

(21) Appl. No.: 13/073,747

(22) Filed: Mar. 28, 2011

(65) Prior Publication Data

US 2011/0190744 A1     Aug. 4, 2011

Related U.S. Application Data

(63) Continuation of application No. 11/937,760, filed on Nov. 9, 2007, now Pat. No. 7,931,644.

(60) Provisional application No. 60/865,342, filed on Nov. 10, 2006.

(51) Int. Cl.
    *A61B 18/18*     (2006.01)
(52) U.S. Cl. ............... 606/5; 606/4; 606/10; 606/12; 128/898
(58) Field of Classification Search ........... 606/4–6, 606/10–12; 351/205–212; 128/898
    See application file for complete search history.

(56) References Cited

U.S. PATENT DOCUMENTS

| | | |
|---|---|---|
| 4,665,913 A | 5/1987 | L'Esperance, Jr. |
| 5,144,630 A | 9/1992 | Lin |
| 5,505,724 A | 4/1996 | Steinert |
| 5,634,920 A | 6/1997 | Hohla |
| 5,646,791 A | 7/1997 | Glockler |
| 5,683,379 A | 11/1997 | Hohla |
| 5,713,892 A | 2/1998 | Shimmick |
| 5,742,626 A | 4/1998 | Mead et al. |
| 5,912,775 A | 6/1999 | Glockler |
| 6,019,755 A | 2/2000 | Steinert |

(Continued)

FOREIGN PATENT DOCUMENTS

WO    97/37622 A1    10/1997

(Continued)

OTHER PUBLICATIONS

Borsutzky et al., "*Tunable UV Radiation at Short Wavelengths (188-240 nm) Generated by Sum-Frequency Mixing in Lithium Borate*", *Appl. Phys.* B 52:380-384 (1991).

(Continued)

*Primary Examiner* — Ahmed Farah
(74) *Attorney, Agent, or Firm* — AMO Manufacturing USA, LLC

(57) ABSTRACT

Systems and methods for removing an epithelial layer disposed over a stromal layer in a cornea irradiate a region of the epithelial layer with a pulsed beam of ablative radiation. The ablative radiation is scanned to vary the location of the beam within the region in accordance with a pulse sequence. The pulse sequence is arranged to enhance optical feedback based on a tissue fluorescence of the epithelial layer. The penetration of the epithelial layer is detected in response to the optical feedback. The use of scanning with the pulse sequence arranged to enhance optical feedback allows large areas of the epithelium to be ablated such that an operator can detect penetration of the epithelial layer.

6 Claims, 14 Drawing Sheets

U.S. PATENT DOCUMENTS

| | | |
|---|---|---|
| 6,203,539 B1 | 3/2001 | Shimmick et al. |
| 6,210,401 B1 * | 4/2001 | Lai .................................. 606/12 |
| 6,245,059 B1 | 6/2001 | Clapham |
| 6,293,939 B1 | 9/2001 | Steinert |
| 6,331,177 B1 | 12/2001 | Munnerlyn et al. |
| 6,347,549 B1 | 2/2002 | Ryan et al. |
| 6,592,574 B1 * | 7/2003 | Shimmick et al. ................. 606/4 |
| 6,613,041 B1 * | 9/2003 | Schrunder .......................... 606/5 |
| 6,984,227 B2 | 1/2006 | Munnerlyn et al. |
| 7,008,415 B2 | 3/2006 | Yee et al. |
| 7,077,838 B2 | 7/2006 | Wong |
| 7,931,644 B2 * | 4/2011 | Arnoldussen et al. ............ 606/5 |
| 2003/0176855 A1 | 9/2003 | Gross et al. |
| 2004/0147910 A1 | 7/2004 | Fujieda |
| 2005/0102008 A1 | 5/2005 | Wong |

FOREIGN PATENT DOCUMENTS

| | | |
|---|---|---|
| WO | 01/08547 A2 | 2/2001 |

OTHER PUBLICATIONS

International Search Report and Written Opinion of PCT Application No. PCT/US2007/084341; dated Mar. 10, 2008, 17 pages total.

U.S. Appl. No. 12/122,319, filed May 16, 2008, first named inventor: Keith Holiday.

U.S. Appl. No. 12/121,635, filed May 15, 2008, first named inventor: Mark Arnoldussen.

* cited by examiner

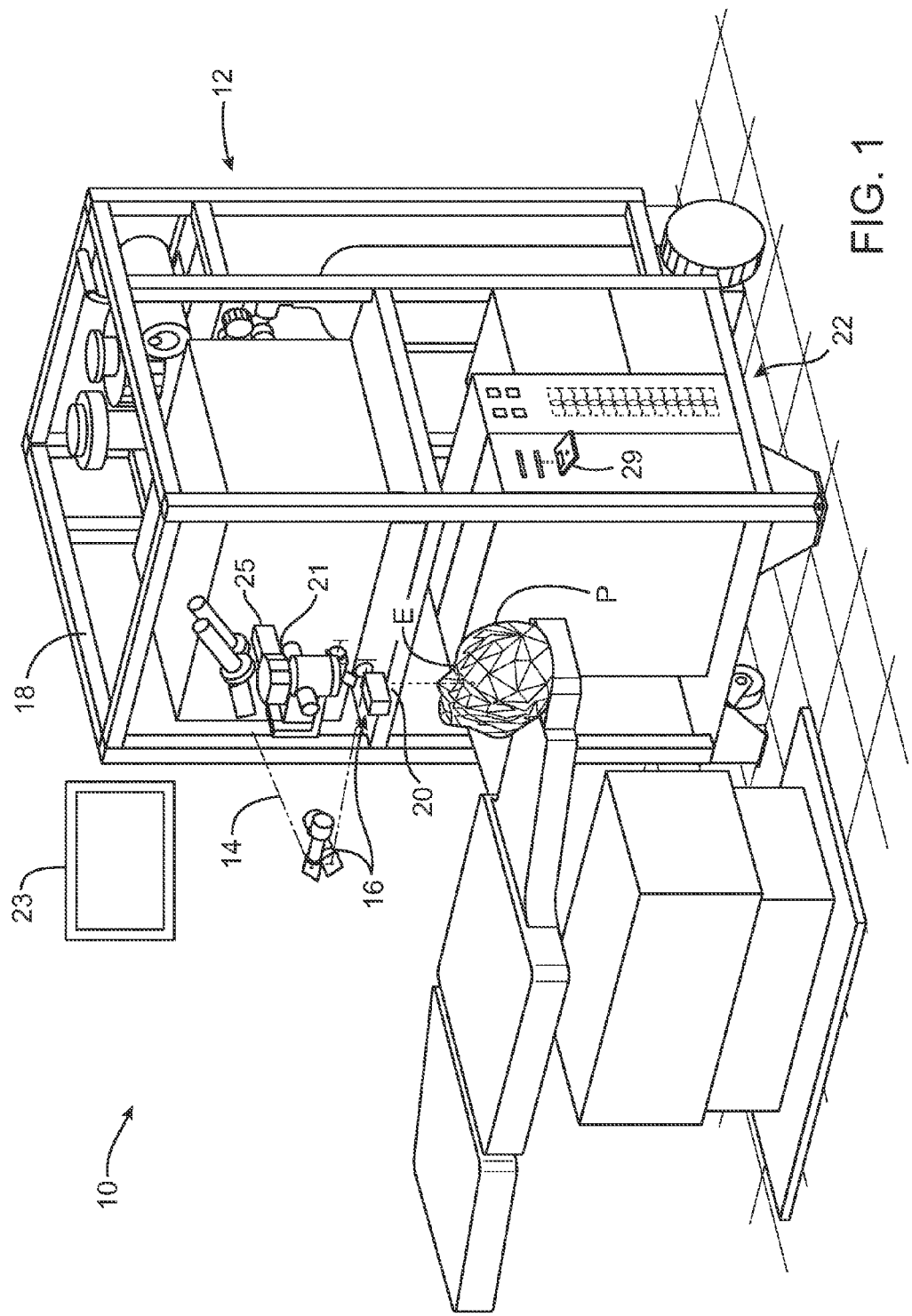

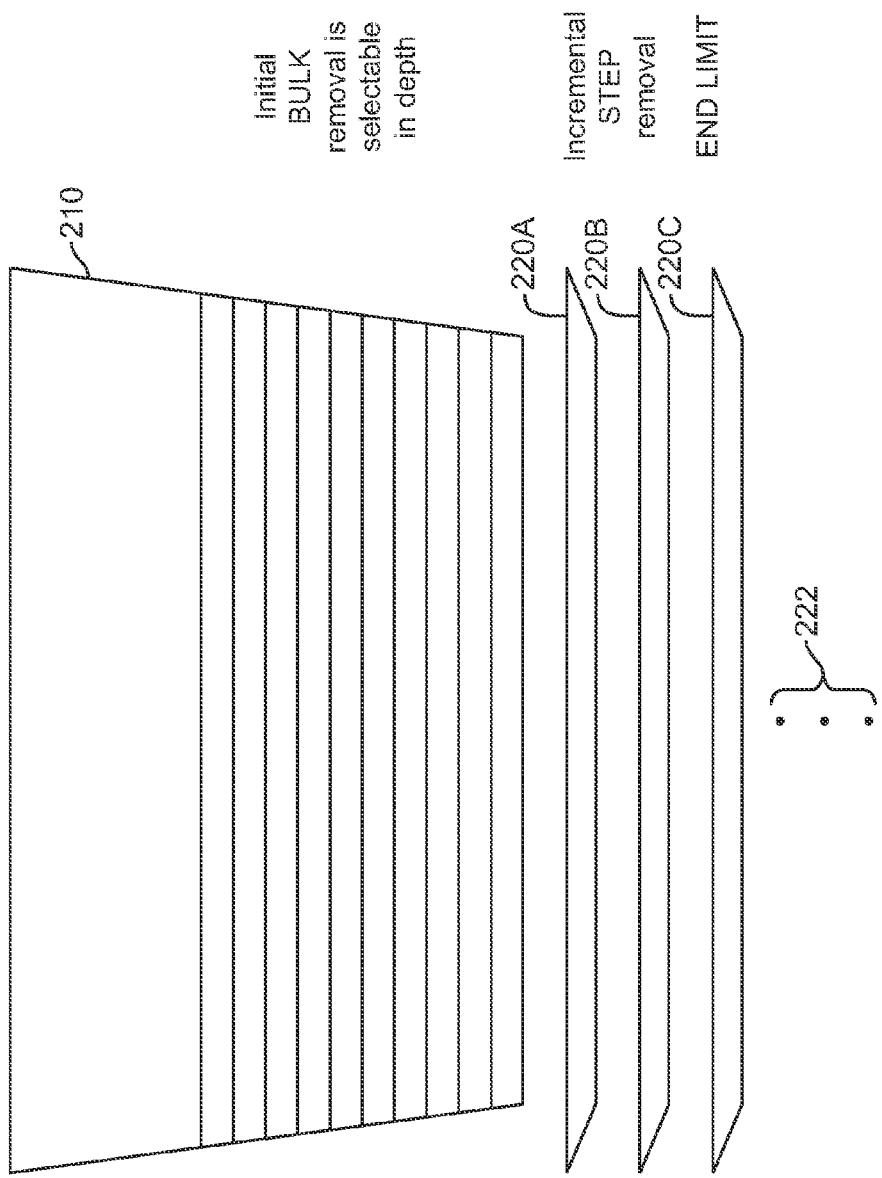

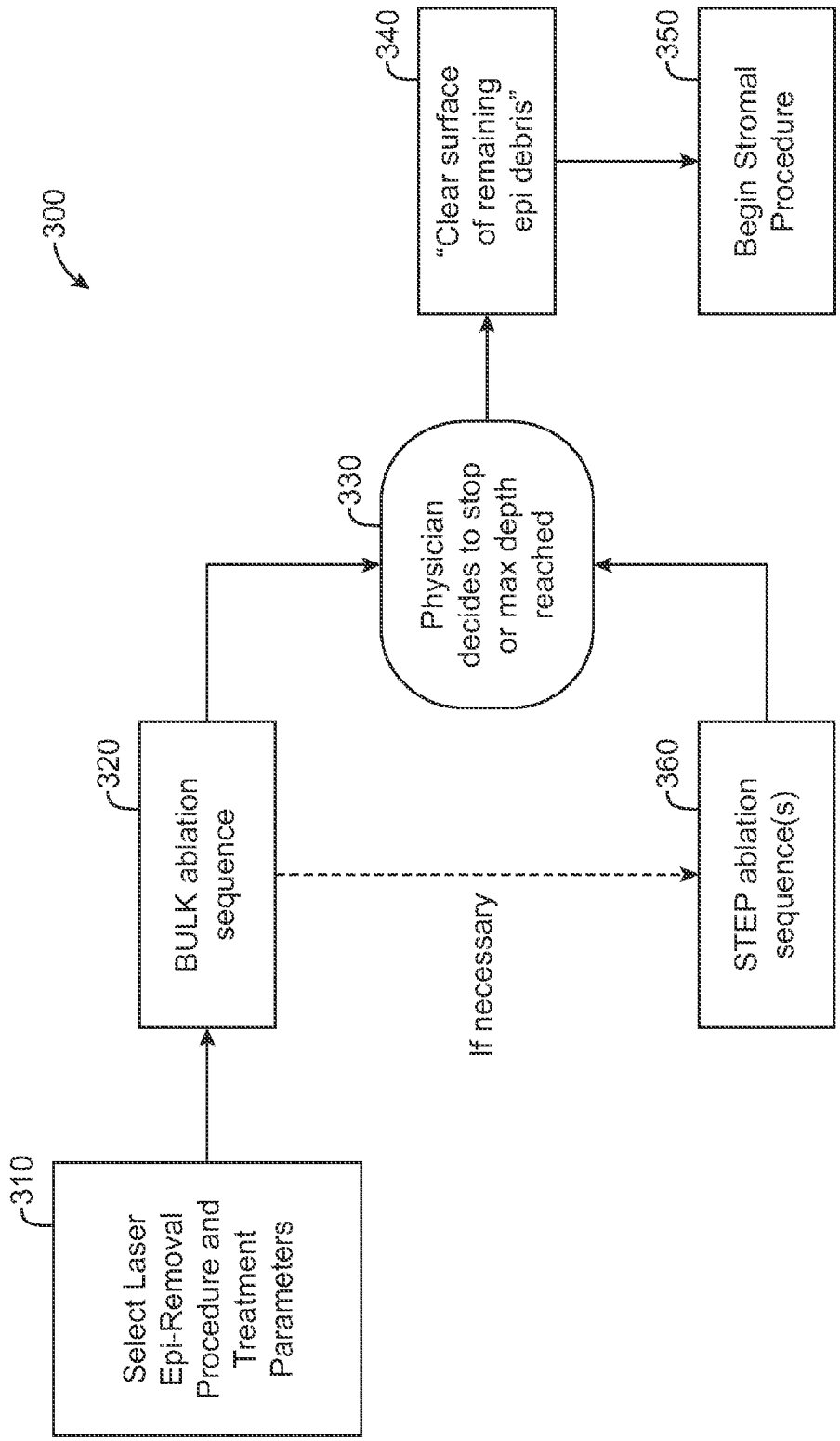

| pulse # | est. depth | Iris (mm) | x (mm) | y (mm) | delay (ms) |
|---|---|---|---|---|---|
| 1 | 0.056249 | 2.75 | -4.4 | 0.5 | 100 |
| 2 | 0.112499 | 2.75 | -1.8 | 4 | 50 |
| 3 | 0.168748 | 2.75 | 2.7 | 2.5 | 50 |
| 4 | 0.224997 | 2.75 | 4.2 | -1.8 | 50 |
| 5 | 0.281247 | 2.75 | 2.6 | -2.8 | 50 |
| 6 | 0.337496 | 2.75 | 0.3 | -4.5 | 50 |
| 7 | 0.393745 | 3 | 0 | 0.2 | 50 |
| 8 | 0.449994 | 3 | -4.3 | 0.9 | 50 |
| 9 | 0.506244 | 3 | -2.9 | 2.8 | 50 |
| 10 | 0.562493 | 3 | 0 | 4.4 | 50 |
| 11 | 0.618742 | 3 | 1.3 | 3.9 | 50 |
| 12 | 0.674992 | 3 | 3 | 3.1 | 50 |
| 13 | 0.731241 | 3 | 4.1 | 1.5 | 50 |
| 14 | 0.78749 | 3 | 4.4 | 0.4 | 50 |
| 15 | 0.84374 | 3 | 3.7 | -1.9 | 50 |
| 16 | 0.899989 | 3 | 2.2 | -3.8 | 50 |
| 17 | 0.956238 | 3 | -0.8 | -4.3 | 50 |
| 18 | 1.01249 | 3 | -2.9 | -3.1 | 50 |
| 19 | 1.06874 | 3 | -3.8 | -1.5 | 50 |
| 20 | 1.12499 | 3 | -4.1 | -0.1 | 50 |
| 21 | 1.18124 | 3.25 | -4.3 | 0.1 | 50 |
| 22 | 1.23748 | 3.25 | -2.7 | 2.8 | 50 |
| 23 | 1.29373 | 3.25 | -1.2 | 3.4 | 50 |
| 24 | 1.34998 | 3.25 | 2.6 | 3.3 | 50 |
| 25 | 1.40623 | 3.25 | 3.3 | 1.9 | 50 |
| 26 | 1.46248 | 3.25 | 4.3 | 0.1 | 50 |
| 27 | 1.51873 | 3.25 | 3.4 | -2.6 | 50 |
| 28 | 1.57498 | 3.25 | 2.4 | -3.4 | 50 |
| 29 | 1.63123 | 3.25 | 1.1 | -4.2 | 50 |
| 30 | 1.68748 | 3.25 | -0.4 | -4.3 | 50 |
| 31 | 1.74373 | 3.25 | -2.2 | -3.7 | 50 |
| 32 | 1.79998 | 3.25 | -3.8 | -2.1 | 50 |
| 33 | 1.85623 | 3.5 | 0.4 | -0.3 | 50 |
| 34 | 1.91248 | 3.5 | -4.1 | 0.2 | 50 |
| 35 | 1.96873 | 3.5 | -3.3 | 2.6 | 50 |
| 36 | 2.02498 | 3.5 | -1.6 | 2.9 | 50 |
| 37 | 2.08122 | 3.5 | -1.6 | 3.6 | 50 |
| 38 | 2.13747 | 3.5 | 0.9 | 4 | 50 |
| 39 | 2.19372 | 3.5 | 3.2 | 2.7 | 50 |
| 40 | 2.24997 | 3.5 | 3.7 | 2 | 50 |
| 41 | 2.30622 | 3.5 | 4.1 | -0.2 | 50 |
| 42 | 2.36247 | 3.5 | 3.2 | -2.2 | 50 |
| 43 | 2.41872 | 3.5 | 0.8 | -4 | 50 |
| 44 | 2.47497 | 3.5 | -1.7 | -3.8 | 50 |
| 45 | 2.53122 | 3.5 | -3.6 | -1.6 | 50 |
| 46 | 2.58747 | 3.5 | -3.8 | -0.1 | 50 |
| 47 | 2.64372 | 3.75 | -2.5 | 1.1 | 50 |
| 48 | 2.69997 | 3.75 | -3.6 | 1.3 | 50 |
| 49 | 2.75622 | 3.75 | -2.7 | 2.7 | 50 |
| 50 | 2.81247 | 3.75 | -1.4 | 3.8 | 50 |
| 51 | 2.86871 | 3.75 | 0.3 | 3.4 | 50 |

FIG. 9

OPERATOR-CONTROLLED SCANNING LASER PROCEDURE DESIGNED FOR LARGE-AREA EPITHELIUM REMOVAL

CROSS-REFERENCES TO RELATED APPLICATIONS

This application is a Continuation of U.S. application Ser. No. 11/937,760 filed Nov. 9, 2007 (Allowed), which application claims the benefit under 35 USC 119(e) of U.S. Provisional Application No. 60/865,342 filed Nov. 10, 2006; the full disclosures, each of which are incorporated herein by reference in their entirety for all purposes.

BACKGROUND OF THE INVENTION

The present invention is generally related to correcting optical errors of light refracted by eyes. In exemplary embodiments, the invention provides devices, systems, and methods for correction of optical errors of eyes, and is particularly well suited for the treatment of eyes during photorefractive keratectomy (PRK) and the like.

Known laser eye surgery procedures generally employ an ultraviolet or infrared laser to remove a microscopic layer of stromal tissue from the cornea of the eye. The laser typically removes a selected shape of the corneal tissue, often to correct refractive errors of the eye. Ultraviolet laser ablation results in photodecomposition of the corneal tissue, but generally does not cause significant thermal damage to adjacent and underlying tissues of the eye. The irradiated molecules are broken into smaller volatile fragments photo-chemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. In known systems, the laser beam often comprises a series of discrete pulses of laser light energy, with the total shape and amount of tissue removed being determined by the shape, size, location, and/or number of laser energy pulses impinging on the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, wavelength multiplied solid-state lasers, and the like. The lasers of these laser systems typically deliver a series of laser beam pulses during a treatment.

Known corneal correction treatment methods have generally been successful in correcting standard vision errors, such as myopia, hyperopia, astigmatism, and the like. By customizing an ablation pattern based on wavefront measurements, it may be possible to correct minor aberrations so as to reliably and repeatedly provide visual acuity greater than 20/20. Such detailed corrections will benefit from an extremely accurate ablation of tissue.

With laser ablation procedures, the epithelium is generally removed so that the permanent optical correction can be ablated into the stroma. With PRK the epithelium is removed to expose Bowman's membrane. Epithelial removal has been accomplished mechanically and with laser ablation of the epithelial layer. Mechanical removal of the epithelial layer can be accomplished with mechanical scraping of the epithelial tissue layer to expose Bowman's membrane. Another mechanical approach is to remove the epithelium with a brush. With Laser-Assisted Sub-Epithelial Keratectomy (LASEK), the epithelial layer is removed from the cornea as a sheet so that the layer can be replaced following the ablation of stromal tissue. Although these mechanical methods of epithelial removal have been successful clinically, mechanical removal of the epithelium takes time and can be perceived by the patients as invasive because the surgeon will touch the front surface of the eye with surgical instruments. Even though topical anesthesia is often applied to the cornea so that the patient cannot feel the surgeon touching his or her cornea, the patient can become nervous while the surgeon touches the front surface of the eye with the instruments, possibly delaying the procedure.

Laser ablation of the epithelium, also referred to as transepithelial ablation, can be less invasive and faster than mechanical approaches to removal of the epithelium. However, work in connection with the present invention suggests that the known methodologies for laser ablation of the epithelium may be less than ideal. Thus, a surgeon will often mechanically scrape the epithelium after laser removal of the epithelium to ensure that no residual epithelial debris remains before ablating stromal tissue.

In light of the above, it would be desirable to provide real-time monitoring of trans-epithelial ablations over large areas of the cornea while avoiding at least some of the limitations of known systems.

BRIEF SUMMARY OF THE INVENTION

Embodiments of the present invention provide improved devices, systems, and methods for laser treatment, for example laser treatment of eyes. More specifically, embodiments of the present invention can enhance the accuracy and efficacy of laser eye surgical procedures with improved removal of the epithelium, for example the corneal epithelium. This improved removal of the corneal epithelium can improve refractive surgical procedures, for example PRK, and can be useful for the therapeutic removal of corneal haze. While the system and methods of the present invention are described primarily in the context of a laser eye surgery system for treating the cornea of the eye, it should be understood that the techniques described herein may be adapted for use in many additional ablation procedures.

Many embodiments use a scanning laser beam that ablates an area larger than the beam and induces fluorescence of the ablated tissue layer, for example the corneal epithelium. A sequence of pulses of the beam is arranged to enhance optical feedback based on the tissue fluorescence so that areas of the epithelium larger than the beam can be ablated and tissue penetration detected. The size and position of the pulse sequence can be arranged to overlap at least some the scanning pulses on a region smaller than the ablation, for example a central region, so that penetration of the epithelium can be detected by viewing the region. Hence, enhanced optical feedback encompasses scanning pulses with a size and position arranged to ablate an area larger than the beam and overlap the pulses on a region, or portion, of the ablated area so that penetration of the epithelium can be detected by viewing the region. In many embodiments an operator may view the region and stop the ablation in response to the enhanced optical feedback, and in some embodiments and energy detector, such as a CCD camera, may view the region ablated pulse sequence arranged to enhance optical feedback.

In a first aspect, embodiments provide a method for removing an epithelial layer disposed over a stromal layer in a cornea. A region of the epithelial layer is irradiated with a pulsed beam of ablative radiation. The ablative radiation is scanned to vary the location of the beam within the region in accordance with a pulse sequence. The pulse sequence is arranged to enhance optical feedback based on a tissue fluorescence of the epithelial layer. The penetration of the epithelial layer is detected in response to the optical feedback.

In many embodiments, the pulse sequence is sorted to enhance the optical feedback. Stromal tissue can be ablated with an optical correction in response the penetration of the epithelial layer.

In many embodiments, the epithelial layer is ablated to a first depth and an additional sub-layer of epithelial tissue is ablated to a second depth in response to the optical feedback.

In specific embodiments, the size of the laser beam is constant while the region is irradiated until the penetration of the epithelium is detected.

In another aspect, embodiments provide a method for removing an epithelial layer disposed over a stromal layer in a cornea. A region of the epithelial layer is irradiated with laser beam pulses of ablative radiation. The ablative radiation is scanned to vary the location of the beam pulses within the region. The beam is adjusted to at least one smaller beam size and at least one larger beam size while the beam is pulsed and scanned over the region in accordance with a pulse sequence arranged to enhance optical feedback. The penetration of the epithelial layer is detected based on tissue fluorescence from the larger sized beam.

In many embodiments, the irradiated region has a central region and an outer peripheral region. The adjustably sized beam can be sized and scanned so that several larger sized pulses comprise marker pulses that overlap, for example in the central region, such that the penetration of the epithelium is detected based on a decrease in fluorescence of the central region from the marker pulses.

In some embodiments, each of the marker pulses covers the central region to provide a measurement signal from the central region. In specific embodiments, the distance across the central region is about 3 mm and each marker pulse is at least about 3.5 mm across so that each marker pulse overlaps and covers the central region. The marker pulses that cover the central region may be delivered at a rate of at least about 1 Hertz to detect penetration of the epithelium.

In many embodiments, the larger beam size has a distance across of at least about 3.5 mm and the smaller beam size has a distance across of no more than about 2.5 mm. In specific embodiments, the adjustably sized beam is circular and the distance across comprises a diameter.

In many embodiments, the distance across the region is at least about 8 mm, and pulses of the larger beam size can comprise at least about 10% of a total number of pulses delivered before the penetration is detected.

In many embodiments, the penetration of the epithelium is detected by an operator based on the visible fluorescence of the epithelial layer irradiated with the large sized pulse.

In some embodiments, the penetration of the epithelium may be detected by an energy detector based on a fluorescence of the epithelial layer irradiated with the larger sized pulse.

In many embodiments, the adjustably sized beam is scanned and sized in accordance with a pre-programmed sequence to vary the location and size of the beam.

In many embodiments, the adjustably sized beam repeatedly changes from at least one smaller size to at least one larger size before the penetration of the epithelium is detected so that the ablated layer of epithelium is substantially uniform when the penetration of the epithelium is detected.

In many embodiments, the adjustably sized beam changes from at least one smaller size to at least one larger size at least about three times, for example five times, before the penetration of the epithelium is detected. In some embodiments, the smaller beam size is no more than about 2.5 mm across and the larger size is at least about 3.5 mm across. In specific embodiments, the smaller size may be no more than about 1.75 mm across and the larger size is at least 4 mm across.

In many embodiments, the adjustably sized beam changes from a smaller size to a larger size in correlation with an intended sub-layer of epithelial tissue ablated. In some embodiments, the intended sub-layer corresponds to an upper portion of the epithelial layer, and the adjustably sized beam changes from the smaller size to the larger size for each additional sub-layer ablated with the adjustably sized laser beam. In specific embodiments, a plurality of the additional sub-layers is ablated before the penetration of the epithelium is detected.

In many embodiments, the tissue fluorescence comprises auto-fluorescence of the tissue that originates from excitation of the molecules of the tissue with the adjustably sized laser beam.

In many embodiments, the adjustably sized beam is sized to provide at least one intermediate beam size having a cross sectional size between the at least the smaller beam size and the larger beam size.

In many embodiments, the adjustably sized beam is repeatedly sized so that the larger size comprises several beam sizes and the smaller size comprises several small beam sizes.

In another aspect, embodiments of the current invention provide a system to ablate an eye to remove an epithelial layer of the eye. A laser generates a beam of an ablative radiation. A movable scan component scans the laser beam over a region of the eye to ablate the epithelial layer. A processor, which comprises a tangible medium and memory, is coupled to the laser and the movable scan component. The processor is configured to scan the beam within the region in accordance with a pulse sequence arranged to enhance an optical feedback signal based on a tissue fluorescence of the epithelial layer.

In many embodiments, the computer is configured to sort the pulse sequence to enhance the optical feedback.

In many embodiments, the system further comprises at least one lens to form an optical image of the fluorescence that is visible to an operator such that the operator can detect the penetration of the epithelial layer based on the optical feedback signal.

In another aspect, embodiments of the current invention provide a system to ablate an eye to remove an epithelial layer of the eye. The system comprises a laser to generate a beam of ablative radiation. A movable structure is disposed along the laser beam path to adjust a size of the laser beam to at least one smaller size and at least one larger size. A movable scan component is configured to scan the laser beam over a region of the eye to ablate the epithelial layer. A processor, which includes tangible medium and memory, is coupled to the laser, the movable structure, and the movable scan component. The processor is configured to ablate an epithelium with at one larger beam size and at least one smaller beam size so that a penetration of the epithelium can be detected based on a tissue fluorescence from the larger size of the beam during a procedure.

In many embodiments, the system comprises at least one of a display or a microscope to provide an image of the tissue fluorescence to an operator so that the operator can detect the penetration of the epithelium.

In some embodiments, the system may include an energy detector to detect the penetration of the epithelium based on the fluorescence.

In many embodiments, the region of the eye comprises a central region and an outer peripheral region. The processor is configured to overlap several pulses of at least one larger size of the beam in the central region to penetrate the epithelium in the central region. In some embodiments, the processor is configured to deliver the pulses with at least one larger size beam to cover the central region to provide a measurement signal from the central region. In specific embodiments, the processor can be configured to deliver pulses of the larger size beam(s) that cover the central region at a rate of at least about 1 Hertz to detect penetration of the epithelium from the measurement signal.

In many embodiments, the processor is configured to scan the laser beam over the region in accordance with a pre-programmed sequence to vary the size and location of the beam. The processor may also be configured to vary between at least one smaller size and at least one larger size to ablate the epithelium at substantially uniform rate. The processor may also be configured to vary the sized beam from at least one smaller size to at least one larger size in correlation with an intended sub-layer of ablated epithelial tissue.

In many embodiments, the small sized beam comprises a substantially circular beam with a diameter no more that about 2 mm across and the large sized beam is circular with a diameter at least about 4 mm across.

In many embodiments, the tissue fluorescence comprises an auto-fluorescence of the tissue that originates from excitation of naturally occurring molecules within tissue in which the molecules are excited with the pulsed laser beam.

In many embodiments, the movable structure may comprise an iris diaphragm, a plurality of apertures formed in a non-transmissive material or a lens.

In many embodiments, the movable scan component may comprise a movable mirror, a movable lens or a movable prism.

BRIEF DESCRIPTION OF THE DRAWINGS

FIG. 1 is a perspective view of a laser ablation system for incorporating the invention;

FIG. 7A shows bulk ablation of a first portion of an epithelial layer and incremental step ablation of additional sub-layers of epithelial tissue, according to embodiments of the present invention;

FIG. 8 shows a method of epithelial ablation, according to embodiments of the present invention; and FIG. 9 shows a treatment table in accordance with an embodiment of the present invention.

DETAILED DESCRIPTION OF THE INVENTION

Figure 1A:
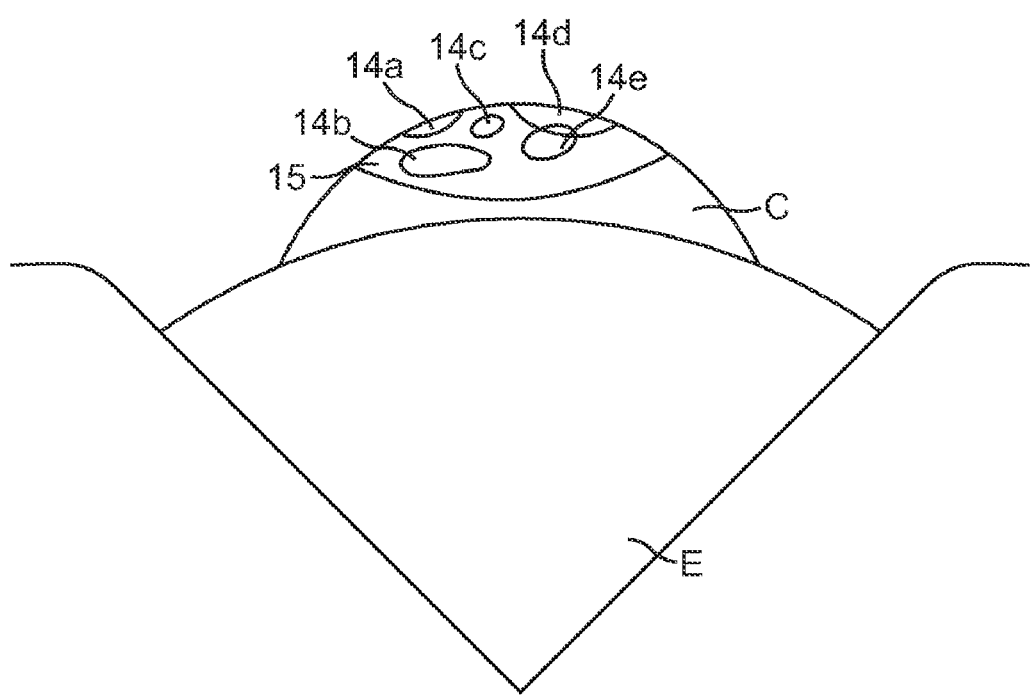
FIG. 1A illustrates an ablation of an epithelial layer of an eye using a series of scanning laser beam pulses of varying diameter applied over a region of a cornea of an eye, according to embodiments of the present invention.

The present invention is particularly useful for enhancing the accuracy and efficacy of laser eye surgical procedures, such as photorefractive keratectomy (PRK), phototherapeutic keratectomy (PTK), and the like. Preferably, the present invention can provide enhanced optical accuracy of refractive procedures and improved patient comfort during the procedure by improving removal of the corneal epithelium. Hence, while the system and methods of the present invention are described primarily in the context of a laser eye surgery system for treating a cornea of the eye, it should be understood the techniques of the present invention may be adapted for use in alternative ablation procedures.

The techniques of the present invention can be readily adapted for use with existing laser systems. By providing a more rapid (and hence, may be less prone to error) methodology for correcting optical errors of an eye, the present invention facilitates sculpting of the cornea so that treated eyes may regularly receive a desired optical correction having improved vision with minimal discomfort to a patient.

As used herein a substantially constant power level encompasses a power level that is stable to within about 25% of an average power level.

Referring now to FIG. 1, a laser eye surgery system 10 for incorporating the present invention includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. An input device 20 is used to align laser system 10 with patient P. A microscope 21 is mounted on the delivery optics support structure, the microscope often being used to image a cornea of eye E. The laser eye surgery system 10 may include a display 23 that provides an image of eye E that is visible to the user. A video camera 25 can be optically coupled to microscope 21 to provide an image of the eye E on the display as seen through the microscope. Microscope 21 may comprise at least one lens to form an optical image of the tissue fluorescence that is visible to the operator such that the operator can detect penetration of the epithelial layer based on the optical feedback. Although a microscope is shown, in some embodiments a camera lens can be used to image the tissue fluorescence, such that the image of the tissue fluorescence can be shown on the display. In various embodiments, the laser eye surgery system 10 includes at least some portions of a Star S3 Active Trak™ Excimer Laser System and/or a STAR S4 IR™ Excimer Laser System with Variable Spot Scanning (VSS™) and WaveScan WaveFront® System available from VISX, INCORPORATED of Santa Clara, Calif.

While the input device 20 is here schematically illustrated as a joystick, it should be understood that a variety of input mechanisms may be used. Suitable input mechanisms may include trackballs, touch screens, or a wide variety of alternative pointing devices. Still further alternative input mechanisms include keypads, data transmission mechanisms such as an Ethernet, intranet, internet, a modem, or the like.

Laser 12 generally comprises an excimer laser, ideally comprising an argon-fluorine laser producing pulses of laser light having a wavelength of approximately 193 nm. The pulse of laser light typically has a fixed pulse duration having a full width half maximum (FWHM) of about 15 nano seconds during a treatment. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. The laser system may include, but is not limited to, excimer lasers such as argon-fluoride excimer lasers (producing laser energy with a wavelength of about 193 nm), solid-state lasers, including frequency multiplied solid-state lasers such as flash lamp and diode pumped solid-state lasers. Exemplary solid state lasers include UV solid state lasers (approximately 193-215 nm) such as those disclosed in U.S. Pat. Nos. 5,144,630 and 5,742, 626; Borsurtky et al., "*Tunable UV Radiation at Short Wavelengths* (188-240 nm) *Generated by Sum Frequency Mixing in Lithium Borate*", *Appl. Phys.* 61:529-532 (1995), and the like. The laser energy may comprise a beam formed as a series of discreet laser pulses. A variety of alternative lasers might also be used. Hence, although an excimer laser is the illustrative source of an ablating beam, other lasers may be used in the present invention.

Laser 12 and delivery optics 16 will generally direct laser beam 14 to the eye E of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible media 29 in the form of a treatment table, and the treatment table may be adjusted according to feedback input into processor 22 from an automated image analysis system (manually input into the processor by a system operator) in response to feedback data provided from an ablation monitoring system feedback system. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. No. 5,683,379, and as also described in co-pending U.S. patent application Ser. Nos. 08/968,380, filed Nov. 12, 1997; and 09/274,999 filed Mar. 22, 1999, the full disclosures of which are incorporated herein by reference.

Still further alternatives are possible, including scanning of the laser beam over a surface of the eye and controlling the number of pulses and/or dwell time at each location, as described, for example, by U.S. Pat. No. 4,665,913 (the full disclosure of which is incorporated herein by reference); using masks in the optical path of laser beam 14 which ablate to vary the profile of the beam incident on the cornea, as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the disclosure of which is incorporated herein by reference. An ablation effluent evacuator/filter, and other ancillary components of the laser surgery system which are not necessary to an understanding of the invention, need not be described in detail for an understanding of the present invention.

Processor 22 may comprise (or interface with) a conventional PC system including the standard operator interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal topography map, a measurement of refraction of the eye, and/or an ablation table.

An ablation of an epithelial layer eye using a series of pulses 14a-14e of a scanning laser beam is illustrated in FIG. 1A. The series of pulses are applied over a trans-epithelial ablation region 15 of a cornea C of an eye E. As illustrated in FIG. 1A pulses 14e and 14d overlap. A dimension across pulse 14c is smaller than a dimension across pulse 14b. The series of pulses 14a to 14e are sequentially applied to eye E in accordance with a treatment table listing the coordinates and sizes of the laser beam for each pulse. An additional ablation procedure can then be ablated into the stromal corneal tissue to provide a refractive correction. In some embodiments, the epithelium can be ablated to remove corneal haze.

Figure 2:
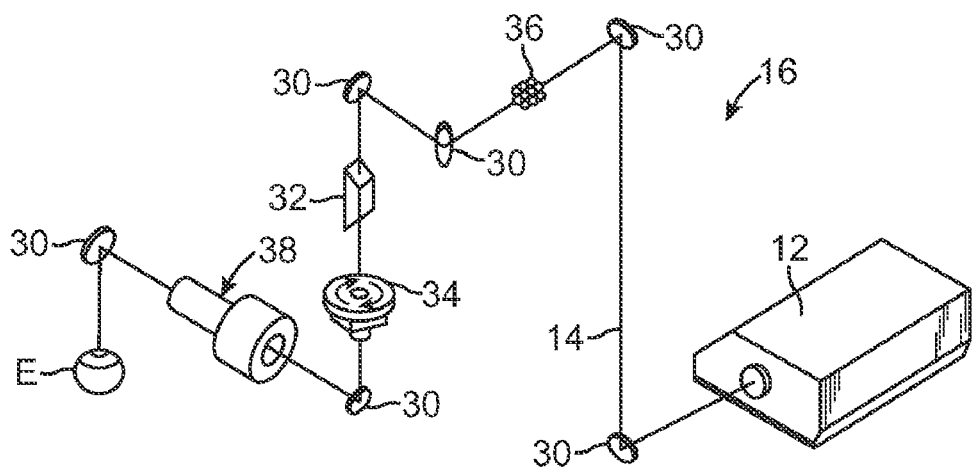
FIGS. 2 and 3 schematically illustrate a laser beam delivery system for selectively directing a laser beam onto the corneal tissue, according to embodiments of the present invention.

Referring now to FIG. 2, laser beam delivery system 16 for directing laser beam 14 at eye E will often include a number of mirrors 30, as well as one or more temporal integrators 32 which may even (or otherwise tailor) the energy distribution across the laser beam. Laser 12 will often comprise an excimer laser as described above.

Figure 3:
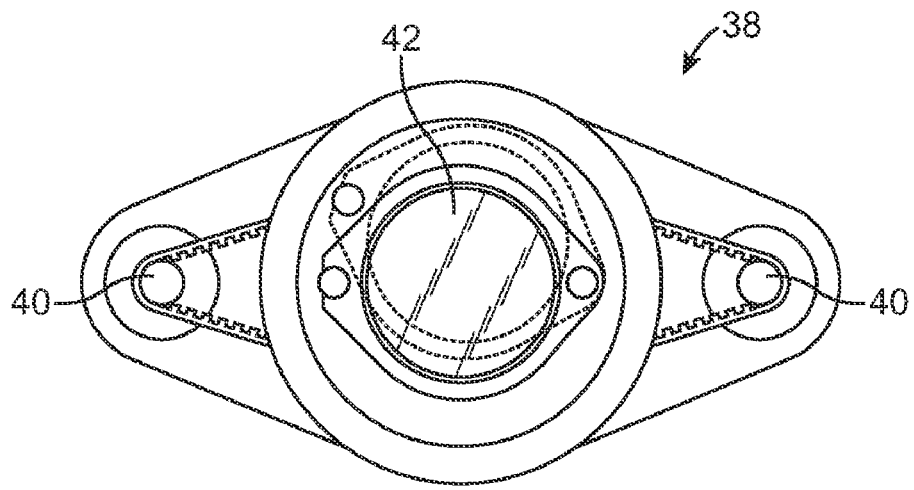

In the exemplary embodiment, a variable aperture 34 changes a diameter and/or slot width to profile laser beam 14, ideally including both a variable diameter iris and a variable width slot. A prism 36 separates laser beam 14 into a plurality of beamlets, which may partially overlap on eye E to smooth edges of the ablation or "crater" from each pulse of the laser beam. Referring now to FIGS. 2 and 3, an offset module 38 includes motors 40 which vary an angular offset of an offset lens 42, and which also change the radial orientation of the offset. Hence, offset module 38 can selectively direct laser beam 14 at a desired lateral region of the cornea. A structure and method for using laser beam delivery system 16 and offset module 38 are more fully described in U.S. Pat. Nos. 6,984,227; 6,331,177; 6,203,539; 5,912,775; and 5,646,791 the full disclosures of which are incorporated herein by reference.

Figure 4:
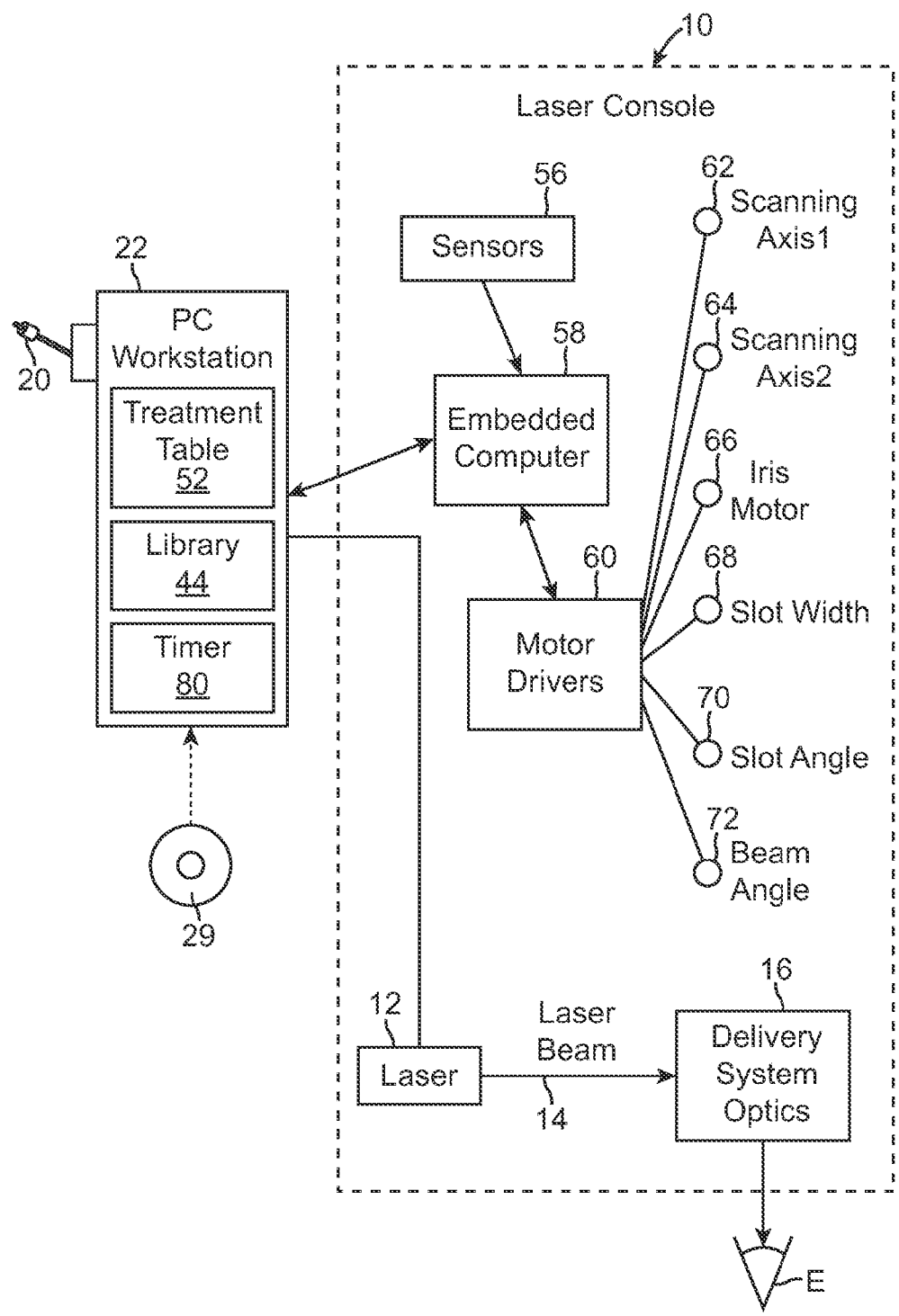
FIG. 4 is a function block diagram illustrating a control architecture of an ablation system as in FIG. 1.

Referring now to FIG. 4, a control system of a laser system 10 is schematically illustrated according to the principles of the present invention. A processor 22 enables precise control of laser system 10 to sculpt a surface shape specified in a laser treatment table 52. A processor 22, which generally comprises a PC workstation, makes use of a computer program stored on a tangible media 29 to generate treatment table 52. Processor 22 includes a library 44 of treatments and treatment tables as described in U.S. Pat. Nos. 6,245,059; and 7,077,838, the full disclosures of which are incorporated herein by reference. An embedded computer 58 within laser system 10 is in electronic communication with the PC workstation. Alternatively, a PC workstation may be embedded in the laser system and include an embedded processor card in communication with the PC workstation for directing the ophthalmic surgery.

Embedded computer 58 is in electronic communication with a plurality of sensors 56 and a plurality of motor drivers 60. The motor drivers 60 are coupled to the embedded computer 58 to vary the position and configuration of many of the optical components of the delivery optics 16 according to treatment table 52. For example, first and second scanning axis 62, 64 control the position of the offset lens to move the beamlets over the surface of the cornea. Iris motor 66 controls the diameter of the overall beam, and in some cases, the length of light transmitted through a variable width slot. Similarly slot width driver 68 controls the width of the variable slot. Slot angle driver 70 controls rotation of the slot about its axis. Beam angle driver 72 controls rotation of the beam as effected by a temporal integrator as described above. Processor 22 issues a command for laser 12 to generate a pulse of the laser beam 14 after the various optical elements have been positioned to create a desired crater on eye E. Treatment table 52 comprises a listing of all of the desired craters to be combined so as to effect a treatment therapy.

A timer 80 is located on an add on card of processor 22 and is a Lab-PC-1200 model card having timers 8253/8254. The Lab-PC-1200 model card is available from National Instruments of Austin, Tex. In alternate embodiments, timer 50 is located externally to processor 22. The timer 80 is controlled by a computer program of processor 22 and is adapted to measure time intervals. The laser 12 is electronically coupled to processor 22. Laser 12 fires upon a command issued from processor 22 in response to a time interval measured by timer 80. Processor 22 varies the rate at which laser 62 fires during at least a portion of a treatment of an eye E.

Figure 5A:
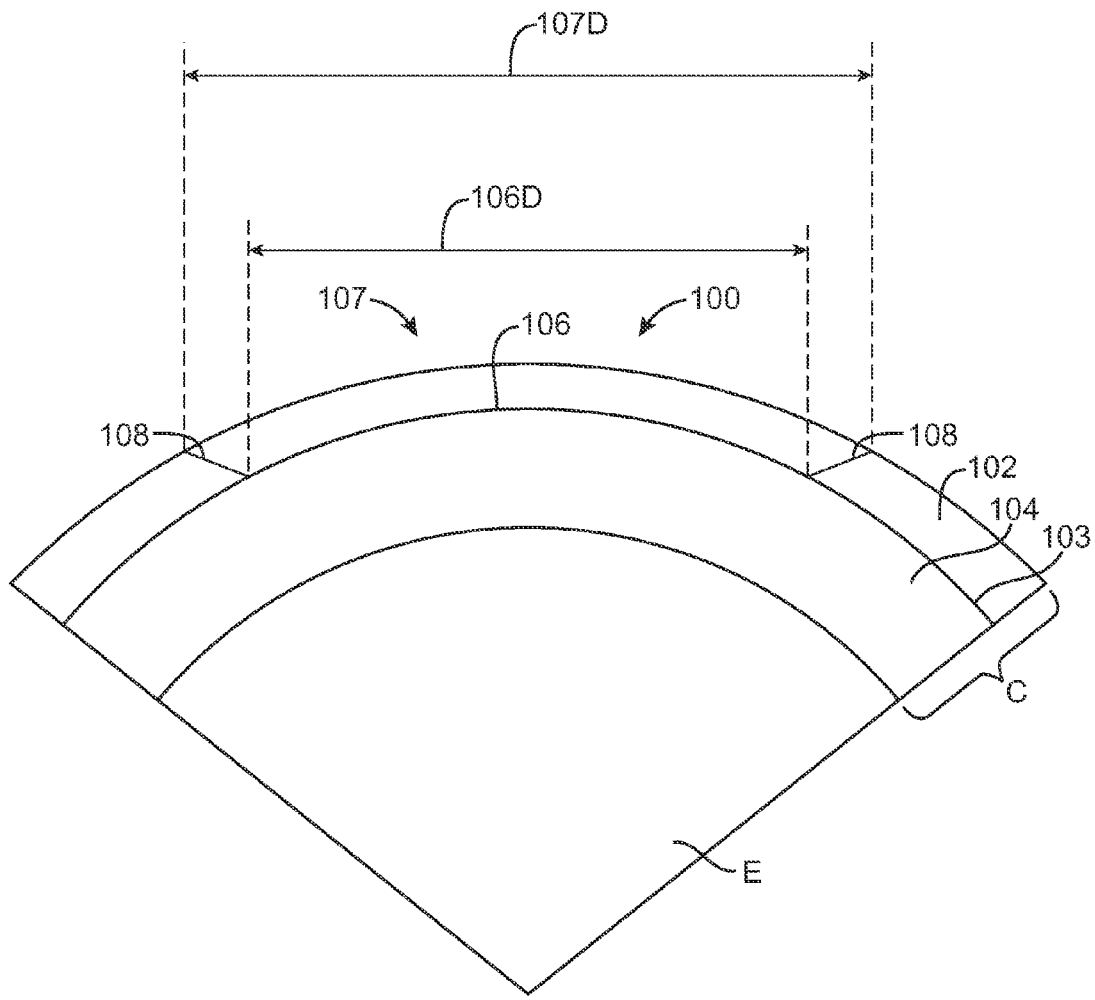
FIG. 5A shows an epithelial ablation profile of an ablated region of an epithelial layer, according to embodiments of the present invention.

FIG. 5A shows an ablation profile 107 of an ablation region 100 of an epithelial layer, according to embodiments of the present invention. Cornea C includes an epithelial layer 102 and a stromal layer 104. A Bowman's membrane 103 is disposed between epithelial layer 102 and stromal layer 104. Ablation profile 107 can include a clearance region 106 in which the epithelium is removed, and a transition zone 108 which extends from clearance region 106 to the unablated regions of the cornea. Transition zone 108 can be annular and extend with a spline, linear fit, or other connecting shape between the unablated epithelium and clearance region 106. Examples of shapes that can be used as transition zones are described in U.S. patent application Ser. No. 10/100,231, filed Mar. 14, 2002, published as US 2003/0176855, the full disclosure of which is incorporated herein by reference. Clearance region 106 can include a diameter across 106D. Ablation profile 107 of ablation region 100 includes transition zone 108 and can include a diameter 107D across ablated region 107. The laser can be programmed to ablate the epithelial layer with a series of laser beam pulses in many ways, for example as described in U.S. Pat. No. 7,008,415, the full disclosure of which is incorporated herein by reference.

The characteristics of epithelial ablation profile 107 can be selected and/or adjusted by the operator as desired, and input with a treatment screen shown on a display as described above. Clearance region 107 can be selected and/or adjusted to many values, for example values from about 8.0 to about 9.5 mm. The maximum ablation zone can be about 2 mm greater than the selected clearance zone to provide an annular transition zone about 1 mm thick. In many embodiments, the width of the annular transition zone as defined from an inner circumference to an outer circumference can be selected to be from about 0.75 to 1.5 mm, although narrower sized transition zones may require addition small laser beam pulses, thereby potentially increasing treatment time. Larger sized transition zones may provide faster tissue removal with larger pulses, although in some embodiments a larger transition zone can cause the ablation to encroach on the limbus. In some embodiments, the maximum ablation width can be limited to about 12 mm. Alternatively or additionally, the maximum ablation width can be based on physiologic measurements from a wavefront machine, topography machine, or the operating microscope, such that the maximum ablation width is 1 mm less than the diameter of the limbus. The maximum depth of ablation can be about 75 microns. The thickness of the epithelial layer can be thicker peripherally than centrally such that the epithelium has a meniscus shape and the operator and/or ablation algorithm can compensate for a thicker peripheral epithelium. The thickness and optical power of the epithelium may also be related to the curvature of the cornea. The curvature of the cornea can be measured with a keratometer and/or topography machine and the keratometer values can be input by the operator and incorporated into the ablation algorithm.

Figure 5B:
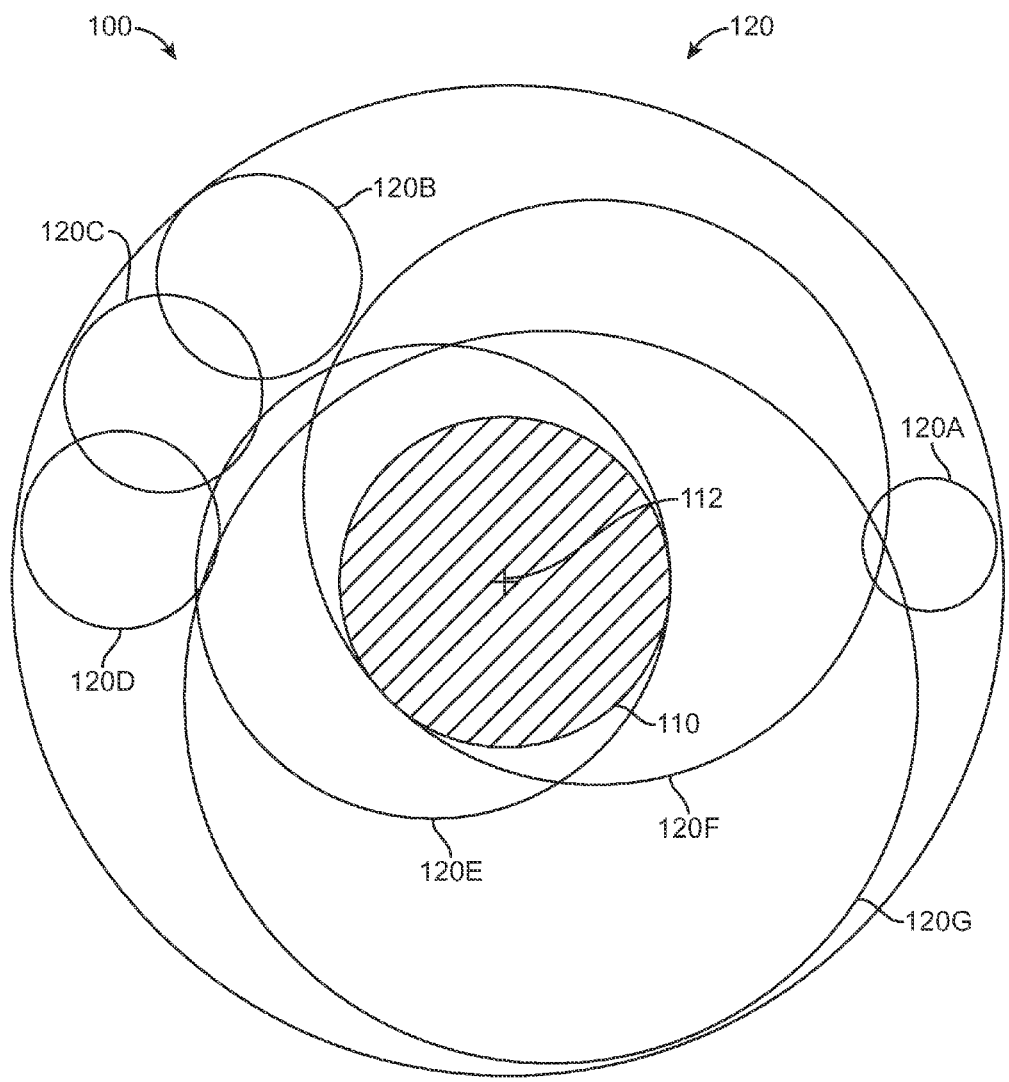
FIG. 5B shows a portion of a sequence of scanning laser beam pulses to used ablate the epithelial layer with the profile of FIG. 5A, in which the pulses are sized and positioned so as to permit detection of a penetration of the epithelial layer, according to embodiments of the present invention.

FIG. 5B shows a portion of a sequence 120 of scanning laser beam pulses to used ablate the epithelial layer with the profile of FIG. 5A, in which the pulses are sized and positioned so as to permit detection of a penetration of the epithelial layer, according to embodiments of the present invention. Although circular pulses are shown, many pulse geometries can be used, for example a variable width slit and/or variable diameter iris diaphragm, and the size of the pulse can refer to a dimension across the pulse, for example a dimension across a slit. Sequence 120 of scanning laser beam pulses can be applied to ablation region 100. Ablation region 100 can include a center 112. Sequence 120 includes individual laser beam pulses 120A to 120G. Laser beam pulses 120A to 120G are sized and positioned in ablation region 100 according to a treatment table. A cross sectional size of each of pulses 120A to 120G can refer to a cross sectional diameter of each of the pulses and position of laser beam pulses 120A to 120G can refer to a position of a center of each pulse in relation to center 112 of ablated region 100. Laser beam pulses 120A to 120D have a small cross sectional size, for example less than about 2 mm. Laser beam pulses 120E to 120G have a large cross sectional size, for example larger than about 3.5 mm. The sequence of laser beam pulses can include additional sizes of laser beam pulses, for example intermediate size pulses having a diameter greater than about 2 mm and less than about 3.5 mm. Laser beam pulses 120E to 120G overlap and cover a central region 110.

Fluorescence from central region 110 can be monitored to detect penetration of the epithelial layer. In many embodiments, the fluorescence that is monitored can comprise tissue auto-fluorescence that results from native molecules of the epithelial layer that are excited with the ablative laser radiation. In some embodiments, the fluorescence can include fluorescence that results from the excitation of a fluorescent dye applied to the epithelium, which fluoresces in response to excitation from the ablative laser radiation. Although overlap is shown in the central region, the pulse sequence can be arranged to overlap and cover other locations of the ablation region, for example peripheral regions, such that optical feedback is enhanced in the peripheral regions where the pulses overlap.

The small size laser beam pulses can include several sizes of laser beam pulses, and the large and intermediate size laser beam pulses can also include several sizes of laser beam pulses. For example, in many treatments the small sized laser beam pulses will comprises several pulses having a diameter from about 0.7 mm to about 2.5 mm, and the large size laser beam pulses will comprise several laser beam pulses having a diameter from about 3.5 to about 6.5 mm. In many embodiments, the laser beam pulses used to ablate the epithelial layer can include several intermediate sized laser beam pulses having a diameter from about 2.5 to 3.5 mm. Small size laser beam pulses can be used to provide accurate ablation of tissue and minimize residual error while medium and large pulses can provide faster tissue removal and permit the user to visualize penetration of the epithelium. In preferred embodiments, small pulses may be used initially followed by large pulses, although the pulse sequence can be sorted in many ways. In some embodiments, a laser beam pulse with a particular size can include several simultaneously generated overlapping laser beams, for example as described in U.S. Pat. No. 6,984,227, previously incorporated herein by reference.

The pulse sequence can be arranged to provide medium to large sized laser beam pulses that overlap in central region 110 to mark the penetration of the epithelium based on a decrease in fluorescence upon penetration of the epithelium. Auto-fluorescence of the epithelial layer is greater than the auto-fluorescence of the underlying stromal layer so that the pulses in central region 110 appear bright initially due to auto-fluorescence of the epithelial layer. Upon penetration into the stromal layer and many instances upon penetration into Bowman's membrane, the auto-fluorescence decreases rapidly so that penetration of the epithelium can be detected. In some embodiments, large laser beam pulses can cover central region 110 so as to permit detection of the penetration of the epithelium. Each of pulses 120E to 120G are sized with a diameter and positioned in ablated region 100 so that each of pulses 120E to 120G covers central region 110. Thus, an operator viewing the ablation of region 100 can detect penetration of the epithelium visually by observing central region 110 and monitoring the tissue fluorescence of central region 110 that results from the marker pulses applied to ablated region 100. In a preferred embodiment central region 110 has a dimension across of about 3 mm, although central region 110 can be from about 2 to 6 mm across. Also, although central region 110 is shown as circular, central region 110 can be hexagonal, triangular nor nearly any other shape that can provide a central region in which the fluorescence pattern appears substantially uniform until the epithelium is penetrated. In some embodiments, marker pulses can be applied to non-central regions of the ablation region, for example to peripheral regions, such that penetration of the epithelium can be detected peripherally with the marker pulses overlapping in the periphery of the ablated region.

The use of large to medium size pulses to mark the penetration of the epithelium can be accomplished in any number of ways. Work in relation with embodiments the present invention suggests that medium to large pulses applied to central region 110 with a frequency of at least about 0.5 Hz can provide a sufficient visual stimulus for an operator to detect penetration of the epithelial layer based on tissue auto-fluorescence in the visible portion of the spectrum of electromagnetic radiation. The marker pulses can be repeated at many frequencies from about 0.5 Hz to about 50 Hz, so that an operator can readily detect penetration of the epithelium based on the auto-fluorescence of the epithelium originating from the central region with the marker pulses. For example, in many embodiments, the marker pulses are repeated at a frequency of about 5 to 20 Hz. In preferred embodiments, about two to three marker pulses can be applied sequentially at about 20 Hz and about 1 second later an additional two to three marker pulses can be applied at about 20 Hz. Thus, the operator can readily visualize a penetrated region of the epithelium with marker pulses spaced no more than one second apart and applied with a frequency of at least about 1 Hz. In many embodiments, large central marker pulses can comprise at least about 5% of the total number of pulses used to ablate the epithelium for example from 5 to 25% of the total number of pulses delivered during ablation of the epithelium. In many embodiments, the large central marker pulses comprise at least about 10% of the total number of pulses used to ablate the epithelium, for example from about 10 to 15% of the total number of pulses applied to ablated the epithelium.

Figure 5C:
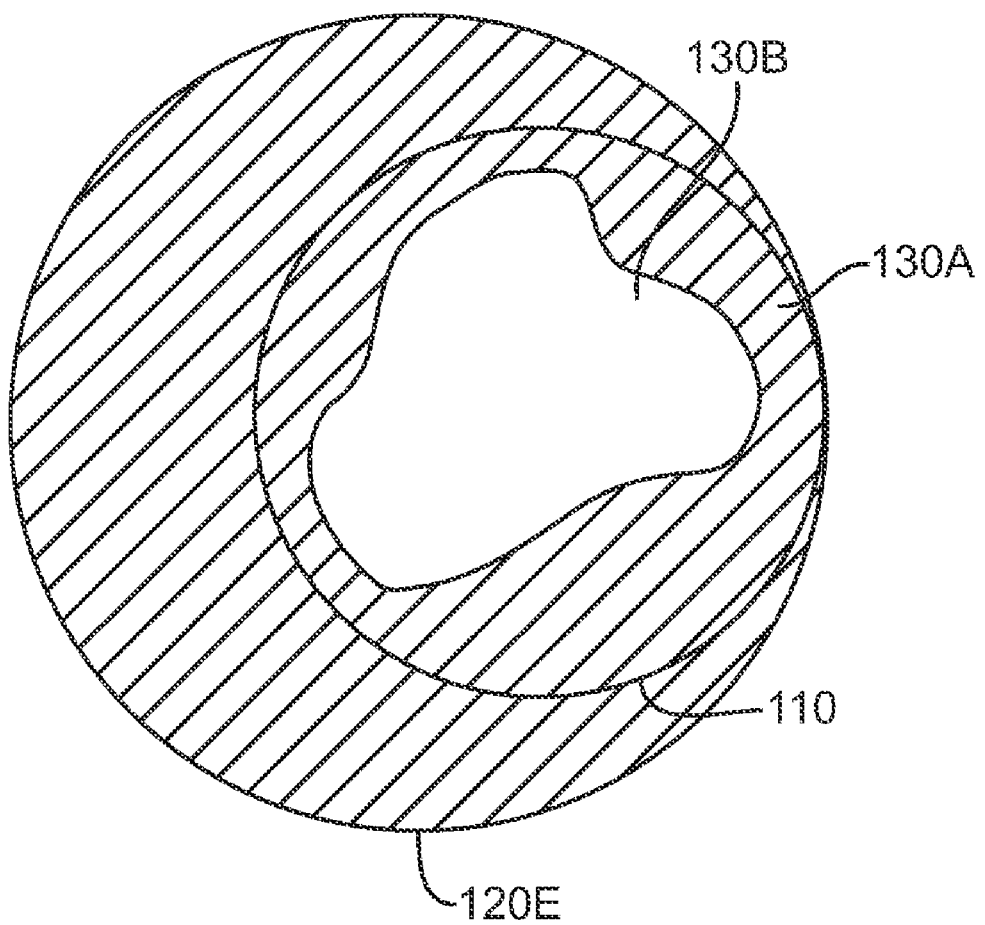
FIG. 5C shows penetration of the epithelial layer with a marker pulse of the sequence as in FIG. 5B, according to embodiments of the present invention.

FIG. 5C shows penetration of the epithelial layer with a marker pulse of the sequence as in FIG. 5B, according to embodiments of the present invention. Central region 110 is covered by pulse 120E. An epithelial fluorescence pattern 130A indicates where the epithelium has not been penetrated. A stromal and/or Bowman's fluorescence pattern 130B indicates where the epithelium has been penetrated. Subsequent pulses 120F and 120G cover central region 110 so that stromal and/or Bowman's fluorescence pattern 130B has substantially the same shape and becomes somewhat larger. Because stromal and/or Bowman's fluorescence pattern 130B has substantially the same shape with sequential pulses, stromal and/or Bowman's fluorescence pattern can be readily identified with the marker pulses to detect penetration of the epithelium. Prior to penetration of the epithelium, central region 110 has a substantially uniform fluorescence intensity which provides a substantially uniform fluorescence pattern within central region 110. Thus, an operator can readily visualize the penetration of the epithelium based on the change in tissue fluorescence within central region 110.

Figure 5D:
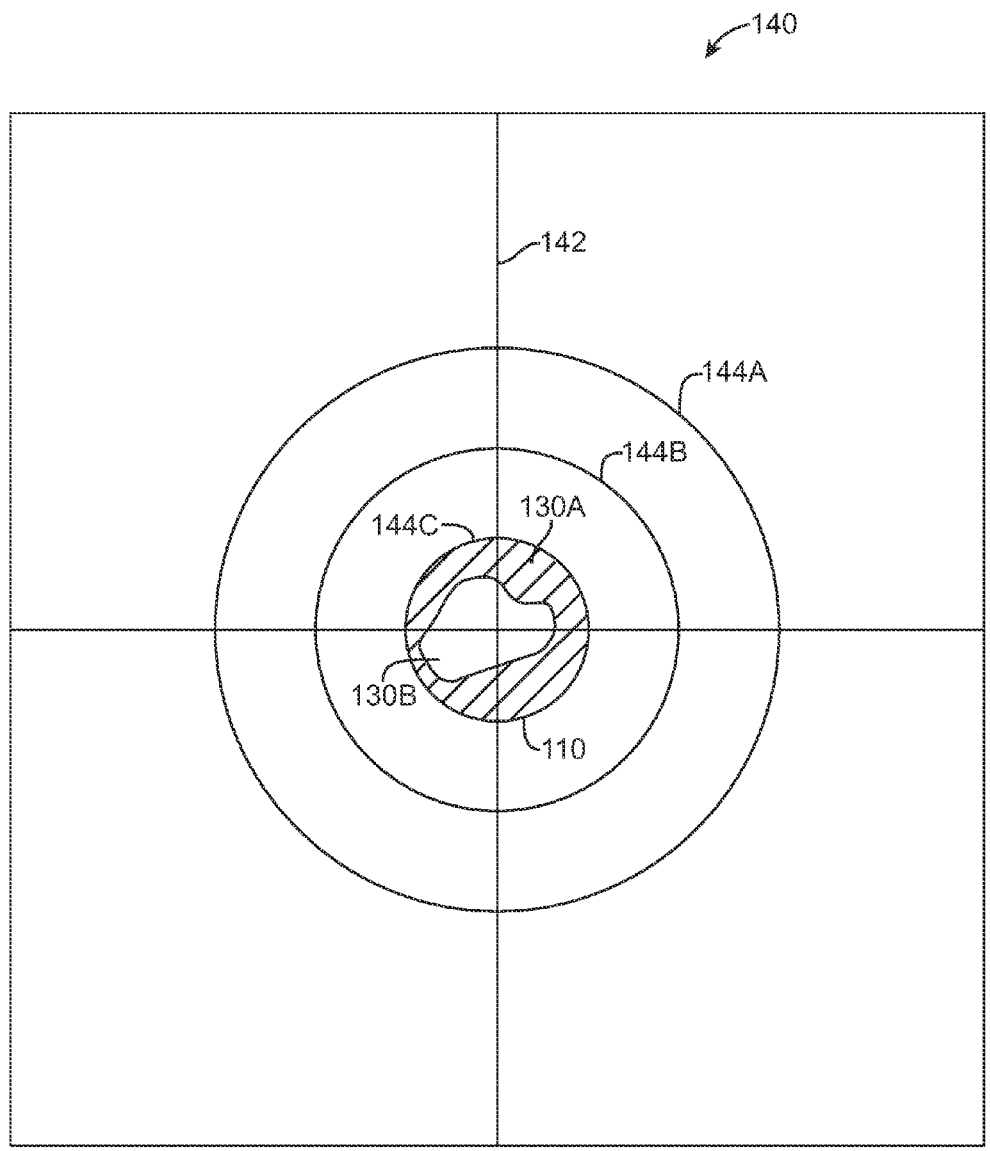
FIG. 5D shows a display visible to a system operator in which the operator can detect penetration of the epithelial layer with the pulses of FIGS. 5B and 5C, according to the embodiments of the present invention.

FIG. 5D shows an optical image 140 of the eye with a fluorescence pattern that is visible to a system operator in which the operator can detect penetration of the epithelial layer with the pulses of FIGS. 5B and 5C, according to the embodiments of the present invention. Optical image 140 can be displayed on a computer display as described above. In many embodiments, optical image 140 can be seen by the operator through an operating microscope as described above. Optical image 140 can include a reticule 142 for alignment of the ablation. Reticule 142 can include concentric circles 144A to 144C. In a preferred embodiment, reticule 144C corresponds to central region 110. The operator observes epithelial fluorescence 130A and can detect penetration of the epithelium based on the appearance of stromal and/or Bowman's ablation pattern 130B. In some embodiments, a detector, for example a CCD that detects optical image 140, can be used with the pulse sequences and optical system as described herein to automate detection of the epithelial penetration and generate an automated optical feedback control signal in response to the penetration of the epithelium. In these embodiments, the detector that detects optical image 140 has a view of eye E. The sorted pulse sequences and optical feedback as described herein can be incorporated into systems that automatically detect penetration of the epithelium to provide control signals, for example as described in U.S. Pat. Nos. 6,293,939; 6,019,755; and 5,505,724; the full disclosures of which are incorporated by reference.

The operator can respond to the visual optical feedback signal in many ways. For example, the operator can terminate the ablation of the epithelium and proceed to ablate the stroma with a desired optical and/or therapeutic correction. The ablation of the stroma can comprise an optical correction such as a wavefront ablation and/or a therapeutic ablation such as the removal of corneal haze. In many embodiments, prior to stromal ablation and after detection of epithelial penetration, the operator may respond to the detection of epithelial penetration by scraping the exposed surface to ensure that all epithelial material has been removed so that any debris that may be present does not effect the stromal ablation process.

In embodiments where epithelial penetration is not detected with a first sequence of pulses, the operator may respond to the optical feed back signal by selecting additional pulses and/or sequence(s) to ablate additional sub-layers of the epithelium. In some embodiments, for example, once a first sequence of pulses corresponding to first ablation depth, for example 50 um, has been applied, the optical feedback signal may indicate that the epithelium has not been penetrated. In response, the operator may select ablation with an additional sequence of pulses corresponding to ablation of an additional layer of epithelial tissue, for example 5um, and ablate this additional layer of tissue while observing the ablation process optical feedback provided by the sorted pulses. This process can be repeated with additional sequences that correspond to the ablation of additional layers, for example in 5 um increments, until penetration is detected in the central region or a total maximum allowed ablation depth, for example 70 um, has been achieved. The first ablation depth corresponding to the first sequence can be from about 30 to about 60 microns, for example 50 um as described above. The additional ablation depth(s) corresponding to the additional sequence(s) can correspond to depths for each layer within a range from about 1 to about 10 microns, for example 5 um as described above. The above pulses sequences can be sorted to enhance optical feedback as described above.

Figure 6A:
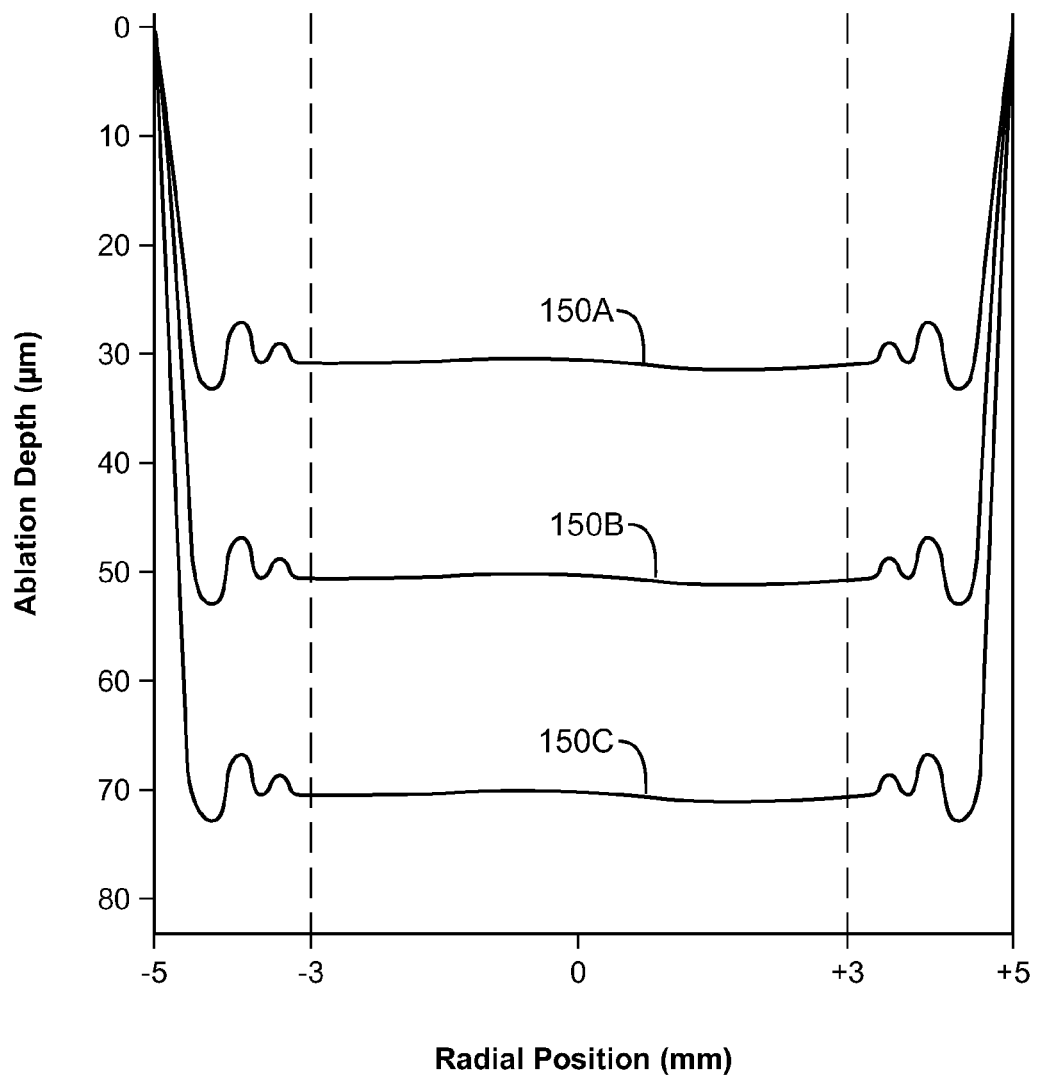
FIG. 6A illustrates theoretical ablation profiles that can be attained upon penetration of the epithelium, according to embodiments of the present invention.

FIG. 6A illustrates ablation profiles that can be attained upon penetration of the epithelium, according to embodiments of the present invention. Upon detection of penetration of the epithelium, the operator can stop the laser ablation of the epithelial surface. Thus, it is desirable that the ablated layer of epithelial tissue is smooth when the operator terminates the ablation of the epithelial surface. Ablation profile 150A shows a theoretical ablation profile that results from the operator stopping the epithelial ablation when the epithelium is penetrated at an average ablation depth of 30 microns. Ablation profile 150B and ablation profile 150C show theoretical ablation profiles for epithelial ablations terminated at average ablation depths of 50 microns and 70 microns respectively. Similar ablation profiles can be achieved for ablations terminated at many depths between 30 and 70 microns.

The ablation algorithm can be designed to provide a sequence of pulses which provide a desired amount of smoothness, based on the purpose of the underlying stromal ablation. Ablation profiles 150A to 150C show a smooth central region that extends about 6 mm across from a radial position of about −3 mm to a radial position of about +3 mm. The smooth central region corresponds to the ablated optical zone in which stromal tissue is ablated with a refractive optical correction. The smoothness of the ablated epithelial shape can have an RMS value of about 3 um or less, for example 2 um, and a peak to valley roughness of about 10 um or less, 5 um or less. The rougher peripheral region corresponds to the ablated transition zone as described above. As the transition zone is ablated may not be used to provide optical correction of stromal tissue, the exactness of the epithelial ablation over the transition zone may be less critical. In some embodiments, the roughness of the ablated transition zone can have a peak to valley roughness of 20 um or less, for example 10 um or less. As the operator may interrupt the ablation at any time, the smoothness of an ablation that is interrupted in response to penetration of the epithelium may be slightly rougher. To minimize the roughness of ablations that are terminated upon penetration of the epithelium, the pulses are arranged accordingly to provide a smooth ablation upon termination. Work in relation with embodiments of the present invention indicates that ablations terminated in response to detection of epithelial penetration can provide smooth surfaces, for example ablation surface having roughness metrics approximately twice those described for ablation to a predetermined depth.

Figure 6B:
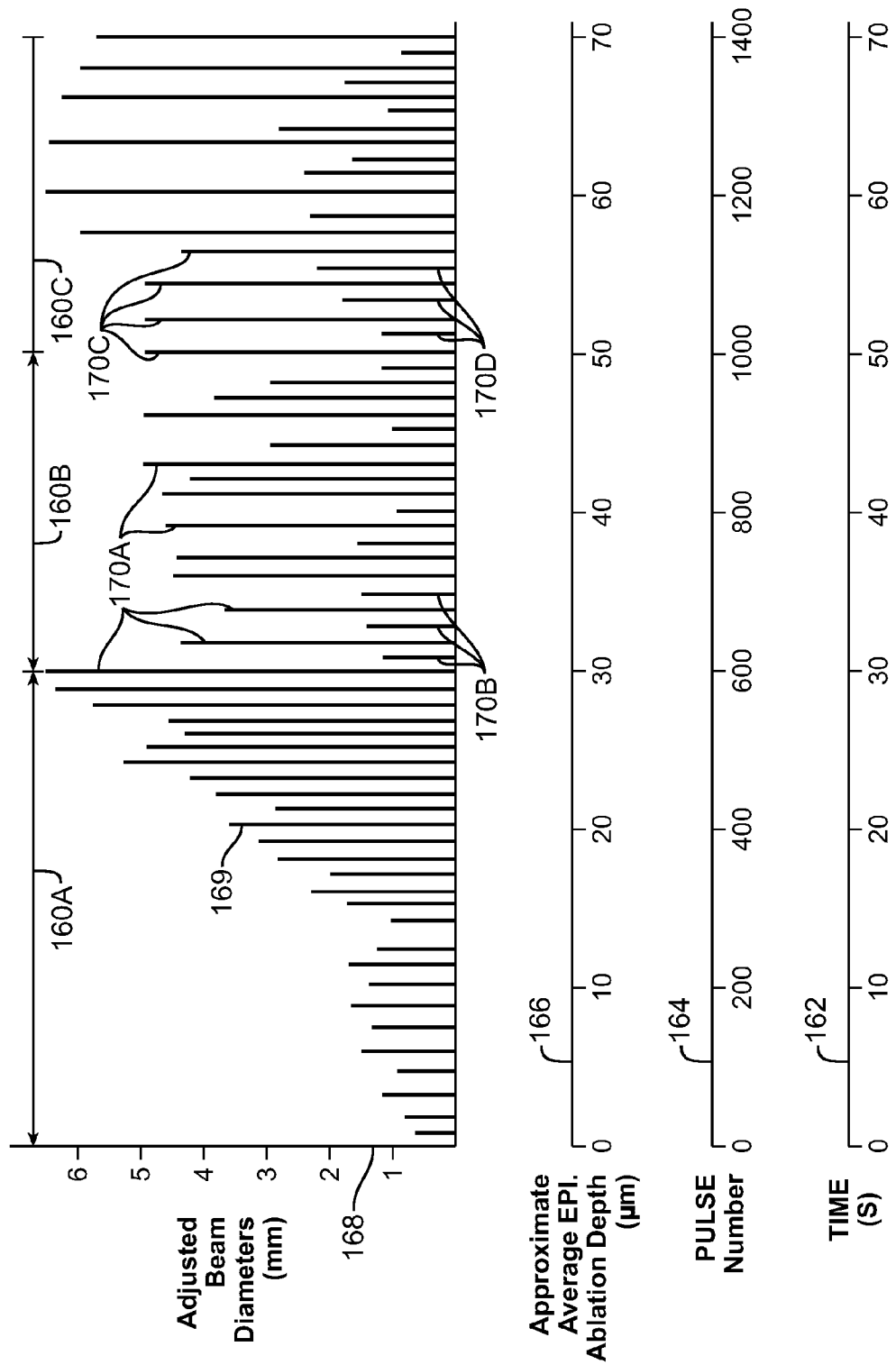
FIG. 6B shows a timing diagram illustrating pulse count, approximate average ablation depth and adjusted laser beam diameter while the laser beam pulses ablate tissue with profiles as in FIG. 6A, according to embodiments of the present invention.

FIG. 6B shows a timing diagram illustrating pulse count, approximate average ablation depth and adjusted laser beam diameter while the laser beam pulses ablate tissue with profiles as in FIG. 6A, according to embodiments of the present invention. The timing diagram includes a treatment time 162 in seconds, a pulse number 164, an approximate average ablation depth 166, and an adjusted beam diameter 168 used to ablate epithelial tissue.

For a laser with a nearly constant laser pulse firing rate, for example 20 Hz, pulse number 164 is closely correlated with treatment time 162. Although pulse number 164 increases linearly with time, in many embodiments it may be desirable to very the laser pulse firing rate by controlling a time delay between each pulse. The average depth of ablation is related to the treatment time and increases with increasing treatment time. In general, the average depth of ablation proceeds at a rate of about 1 micron per second, although slower rates can be clinically effective and acceptable.

A vertical line 169 shows adjusted beam diameter 168 for several pulses. As will be appreciated with reference to pulse number 164 and vertical line 169, vertical line 169 indicates the size of the laser beam for several pulses of the laser beam, for example about 20 pulses of the laser beam from the 400th pulse to the 420th pulse of the sequence. Thus, each vertical line that corresponds to adjusted beam diameter 168 represents several laser beam pulses of the same diameter, and these laser beam pulses of the same diameter can be scanned to different locations over the ablation region in accordance with the coordinate references of the treatment table.

Adjusted laser beam diameter 168 varies during the ablation of the epithelium. Adjusted laser beam diameter 168 includes several diameters used to ablate the first 30 microns of tissue and these diameters are indicated by arrow 160A. As the epithelial tissue layer is usually no less than 30 microns thick, laser beam pulses of increasing diameter are used to ablate the first 30 microns of tissue. If the operator terminates the ablation at a depth of 30 microns ablation profile 150A will be smooth as shown above.

Adjusted laser beam diameter 168 includes several diameters used to ablate epithelial tissue from an average depth of 30 microns to an average depth of 70 microns are indicated by arrow 160B and arrow 160C. As the epithelial tissue layer can be from 30 to 70 microns thick, laser beam pulses of alternating and/or interleaved large and small sizes can be used to ablate the epithelial tissue layer from 30 microns to 70 microns. Arrow 160B shows beam sizes for ablation from a depth of 30 to 50 microns, and arrow 160C shows ablation from a depth of 50 to 70 microns. From 30 to 50 microns, large diameter marker pulses 170A are applied to detect penetration of the epithelium, and small diameter pulses 170B are applied between marker pulses 170A to ensure that the ablation profile is smooth when the operator terminates ablation of the epithelium at a depth based on the detected penetration. From 50 to 70 microns, large diameter marker pulses 170C are applied to detect penetration of the epithelium, and small diameter pulses 170D are applied between marker pulses 170C to ensure that the ablation profile is smooth when the operator terminates ablation of the epithelium at a depth based on the detected penetration. If the operator terminates the ablation at any average ablation depth from 30 microns to 70 microns, the ablation profile will be smooth as shown above. Large beam sizes are used to remove tissue rapidly and provide marker pulses as described above, and the small beam pulses are interleaved between the marker pulses to knock down any non-uniformities in the ablation pattern that develop as the ablation proceeds.

FIG. 7A shows bulk ablation of a first portion 210 of an epithelial layer and incremental step ablation of additional sub-layers 220A to 220C of epithelial tissue, according to embodiments of the present invention. First portion 210 of the ablated epithelial tissue can have a depth of approximately 50 microns, which corresponds to a typical thickness of the ablated epithelial layer. In some embodiments, the operator can program the bulk portion to have a selectable depth in a range from about 20 to 70 microns, for example from about 25 to 60 microns. Additional sub-layers 220A to 220C can be sequentially ablated. Additional sub-layers 222 can be ablated as needed until penetration of the epithelium is detected. Each additional sub-layer has a thickness of approximately 1 to 10 microns, for example about 5 microns. Upon completion of ablation of the bulk layer sequence, the operator can program the laser to ablate an additional sub-layer if penetration is not detected with ablation by the bulk sequence.

Figure 7B:
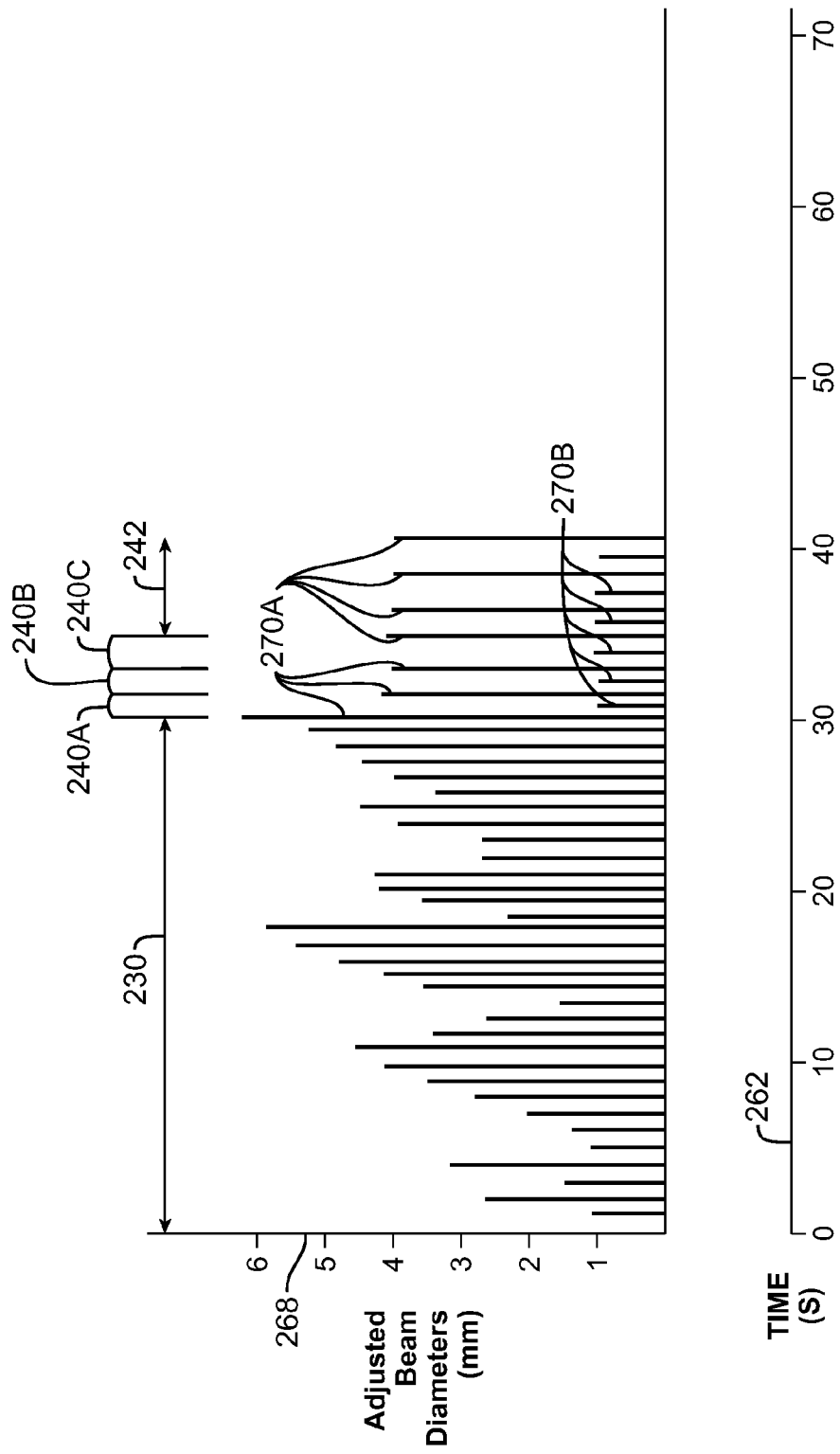
FIG. 7B shows a timing diagram illustrating approximate average ablation depth and adjusted laser beam diameter while the laser beam pulses ablate a first portion of the epithelial layer and additional sub-layers of epithelial tissue as in FIG. 7A, according to embodiments of the present invention.

FIG. 7B shows a timing diagram illustrating approximate average ablation depth and adjusted laser beam diameter while the laser beam pulses ablate a first portion of the epithelial layer and additional sub-layers of epithelial tissue as in FIG. 7A, according to embodiments of the present invention. The timing diagram includes a treatment time 262 in seconds and an adjusted beam diameter 268 used to ablate epithelial tissue. Adjusted laser beam diameter 268 varies during the ablation of the epithelium. Adjusted laser beam diameter 268 includes several diameters used to ablate first portion 210 and these diameters are indicated by arrow 230. As the epithelial tissue layer is usually no less than 30 microns thick, first portion 210 often corresponds to an ablation depth of 30 microns, and laser beam pulses of increasing diameter are used to ablate first portion 210. When the operator terminates the ablation, the ablation profile will be smooth as shown above. In some embodiments, when an operator terminates the ablation during ablation of a sub-layer of the epithelium, the laser may continue the ablation until the ablation of the sub-layer is completed so that the ablation is uniform. Thus, it may be desirable to make the sub-layers thin so that the ablation of the entire sub-layer provides an acceptably thin ablation of the underlying stromal tissue and/or Bowman's membrane.

Adjusted laser beam diameter 268 includes several diameters used to ablated sub-layers 220A to 220C. As the epithelial tissue layer can be from 30 to 70 microns thick, laser beam pulses of alternating and/or interleaved large and small sizes can be used to ablate each of the epithelial tissue sub-layers 220A to 220C. Large diameter marker pulses 270A can be applied to detect penetration of the epithelium, and small diameter pulses 270B can be applied between marker pulses 270B to ensure that the ablation profile is smooth when the operator terminates ablation based on the detected penetration of the epithelial layer. An arrow 242 indicates ablation of epithelial tissue with additional sub-layers 222 at depths below those of sub-layers 220A to 220C. Large and small pulses can be used to ablate each additional sub-layer so that the ablation is smooth when the operator terminates the epithelial ablation in response to penetration of the epithelium.

It should be noted that although FIGS. 5B to 7B make reference to embodiments in which laser beams of varying size are used to ablate the epithelium, embodiments of the present invention can employ a fixed diameter treatment beam to ablate the epithelium. Such embodiments can be readily implemented on the VISX Star™ platform by constraining the treatment table to provide a single fixed constant diameter laser beam during the ablation of the epithelial. The treatment table can be sorted to provide enhanced optical feedback in the central region of the epithelial ablation. This sorting of predetermined fixed diameter laser beam sequences can also be incorporated into laser systems such as those described in U.S. Pat. Nos. 6,635,051; 6,575,962; 6,090,110; and 5,827,264, the full disclosures of which are incorporated herein by reference. Although these embodiments that employ a constant size laser beam are within the scope and spirit of the present invention, work in relation with the present invention suggests that the variable beam embodiments described herein can provide faster ablations with improved optical feedback and improved ablation characteristics, for example smoother ablation surfaces with well defined transition zones and well defined ablation boundaries. In addition or in combination, it should be noted that solid state lasers can also be used to provide sorted ablation sequences with improved optical feedback.

FIG. 8 shows a method of epithelial ablation 300, according to embodiments of the present invention. A step 310 selects laser epithelial removal and treatment parameters. Example parameters include a clearance zone diameter, a total ablation diameter, and a bulk ablation depth, for example 50 microns. A step 320 applies a bulk ablation sequence of laser beam pulses. A step 330 terminates and/or pauses ablation of the epithelial layer in response to detection of penetration of the epithelial layer and/or in response to completion of the bulk ablation sequence so that the epithelium has been uniformly ablated to the selected bulk ablation depth. If necessary, a step 360 selects an additional step ablation sequence, for example a sequence that ablates a 5 micron sub-layer of epithelial tissue. Step 330 terminates and/or pauses ablation of the epithelium in response to detection of penetration of the epithelial layer and/or completion of the additional sub-layer ablated. Additional step sequences can be selected with step 360 and the ablation can be terminated and/or paused at step 330 as many times as needed to detect penetration of the epithelium and/or a maximum ablation depth, for example 70 um It should be appreciated that the specific steps illustrated in FIG. 8 provide a particular method of measuring flow characteristics of a free stream according to an embodiment of the present invention. Other sequences of steps may also be performed according to alternative embodiments. For example, alternative embodiments of the present invention may perform the steps outlined above in a different order. Moreover, the individual steps illustrated in FIG. 8 may include multiple sub-steps that may be performed in various sequences as appropriate to the individual step. Furthermore, additional steps may be added or removed depending on the particular applications. One of ordinary skill in the art would recognize many variations, modifications, and alternatives.

FIG. 9 shows a treatment table 900 in accordance with an embodiment of the present invention. Treatment table 900 includes several parameters to control the pulse size, location and delay for each pulse of the laser beam. A pulse number 910 indicates the pulse number of the sequence. An estimated depth 920 corresponds to the estimated average ablation depth for each pulse number. An iris diameter 930 indicates that diameter of the laser beam on the eye for each pulse of the laser beam. An x-coordinate 940 lists the x-coordinate location on the center of the sized laser beam on the eye for each pulse of the laser beam. A y-coordinate 950 lists the y-coordinate of the center of the sized laser beam on the eye for each pulse of the laser beam. A delay 960 lists the delay from the previous pulse for each pulse of the laser beam, so that the laser pulse repetition rate can be controlled for each pulse of the laser beam. For example delay 960 listed as 50 ms corresponds to a laser firing rate of 20 Hz, and delay 960 listed as 100 ms corresponds to a laser firing rate of 10 Hz. Appendix A, incorporated herein by reference, lists the entire treatment table 900 to an average ablation depth of about 63 microns for about 1100 pulses.

While the present invention has been described with respect to particular embodiments and specific examples thereof, it should be understood that other embodiments may fall within the spirit and scope of the invention. The scope of the invention should, therefore, be determined with reference to the appended claims along with their full scope of equivalents.

What is claimed is:

1. A method for removing an epithelial layer disposed over a stromal layer in a cornea, the method comprising:
   irradiating a region of the epithelial layer with a pulsed ablation beam of an ablative radiation such that the pulsed ablation beam ablates the epithelium;
   scanning the ablative radiation to vary a location of the ablation beam within the region in accordance with an ablation pulse sequence, wherein the ablation pulse sequence is sorted to enhance an optical feedback of the pulsed ablation beam based on a tissue fluorescence of the epithelial layer in response to the ablative radiation; and
   detecting a penetration of the epithelial layer in response to the optical feedback.

2. The method of claim 1 wherein stromal tissue is ablated with an optical correction in response the penetration of the epithelial layer.

3. The method of claim 1 wherein the epithelial layer is ablated to a first depth and an additional sub-layer of epithelial tissue is ablated to a second depth in response to the optical feedback.

4. The method of claim 1 wherein a size of the laser beam is constant while the region is irradiated until the penetration of the epithelium is detected.

5. A system to ablate an eye to remove an epithelial layer of the eye, the system comprising:
   a laser to generate an ablation beam of an ablative radiation;
   a movable scan component to scan the laser ablation beam over a region of the eye to ablate the epithelial layer; and
   a processor comprising a tangible medium and a memory, the processor coupled to the laser and the movable scan component, the processor configured to scan the ablation beam within the region in accordance with a pulse sequence, and wherein the processor is configured to sort the pulse sequence of the ablation beam to enhance an optical feedback and wherein the pulse sequence is arranged when sorted to enhance an optical feedback signal based on a tissue fluorescence of the epithelial layer in response to the ablative radiation.

6. The system of claim 5 further comprising at least one lens to form an optical image of the fluorescence that is visible to an operator such that the operator can detect the penetration of the epithelial layer based on the optical feedback signal.

* * * * *